United States Patent [19]

Nakamura et al.

[11] Patent Number: 5,698,730

[45] Date of Patent: Dec. 16, 1997

[54] METHOD FOR PREPARING CYANOACETIC ACID HIGHER ESTER

[75] Inventors: Katsumi Nakamura; Yasuyuki Takayanagi; Masaaki Seya, all of Yokohama, Japan

[73] Assignee: Nitto Chemical Industry Co., Ltd., Tokyo, Japan

[21] Appl. No.: 769,702

[22] Filed: Dec. 18, 1996

Related U.S. Application Data

[62] Division of Ser. No. 507,258, Aug. 17, 1995, Pat. No. 5,637,752.

[30] Foreign Application Priority Data

Dec. 20, 1993 [JP] Japan ................................. 5-344466
Jun. 16, 1994 [JP] Japan ................................. 6-156406

[51] Int. Cl.$^6$ ........................................... C07C 255/19
[52] U.S. Cl. ................................................. 558/443
[58] Field of Search ..................................... 558/443

[56] References Cited

U.S. PATENT DOCUMENTS

3,773,808  11/1973  Wesselman ..................... 260/465.4

FOREIGN PATENT DOCUMENTS

| 1951032 | 5/1970 | Germany . |
| 2403483 | 8/1975 | Germany . |
| 47-31291 | 8/1972 | Japan . |
| 63-255247 | 10/1988 | Japan . |

OTHER PUBLICATIONS

Helv. Chim. Acta., 42, 1214 (1959).
J. Am. Chem. Soc., 64, 2271–2274 (1942).
J. Chem. Soc., 423–429 (1955).
Org. Synth. Coll., vol. 5, 171 (1973).
Annales de Chimie (Paris), 9 (9), 69 (1918).
Studies in Mass Spectrometry, Tetrahedron, 23, 305 (1967).
Diisopropyl (2S,3S)–2,3–OIsopropylidenetartrate, Org. Synth., 65, 230 (1987).
Helv. Chim. Acta., 65, 1197 (1982).
Helv. Chim. Acta., 65, 495 (1982).
Titanate–Mediated Transesterifications with Functionalized Substraes, Synthesis, 138 (1982).
Chimia, 28 (5), 234–235 (1974).
Chemical Abstracts, 82: 169976b (1982).

*Primary Examiner*—Johann Richter
*Assistant Examiner*—Ebenezer Sackey
*Attorney, Agent, or Firm*—Cushman Darby & Cushman IP Group of Pillsbury Madison & Sutro LLP

[57] ABSTRACT

A cyanoacetic acid higher ester represented by the general formula: $NCCH_2COOR'$, wherein R' represents an alkyl group having 4 to 20 carbon atoms, is prepared by subjecting a cyanoacetic acid ester represented by the general formula: $NCCH_2COOR^1$, wherein $R^1$ represents an alkyl group having 1 to 3 carbon atom, to a transesterification with an alcohol represented by the general formula: R'OH, wherein R' represents an alkyl group having 4 to 20 carbon atoms, in the presence of a specific tin compound as the catalyst. According to the present invention, the cyanoacetic acid higher esters which are useful as intermediates for pharmaceuticals and agricultural chemicals as well as intermediates for industrial products can be prepared easily and in higher yield as compared with conventional methods, by using a cyanoacetic acid ester and an alcohol which are less expensive and easily available as raw materials.

5 Claims, No Drawings

METHOD FOR PREPARING CYANOACETIC ACID HIGHER ESTER

This is a divisional of U.S. application Ser. No. 08/507,258, filed Aug. 17, 1995 (allowed Oct. 1, 1996) now U.S. Pat. No. 5,637,752.

TECHNICAL FIELD

The present invention relates to a method for preparing cyanoacetic acid higher esters which are useful as intermediates for pharmaceuticals and agricultural chemicals and as intermediates for industrial products.

Expression of the cyanoacetic acid higher ester used in the present specification means a cyanoacetic acid ester represented by the general formula: $NCCH_2COOR'$, wherein R' represents an alkyl group having 4 to 20 carbon atoms.

BACKGROUND ART

As to methods for preparing cyanoacetic acid esters, there have been generally well known various methods, such as a method of reacting a chloroacetic acid ester with NaCN or KCN; a method of reacting a cyanoacetyl halide with an alcohol in the presence of a basic catalyst; a method of alkoxycarbonylation by reacting a chloroacetonitrile with CO and an alcohol; a method of subjecting a cyanoacetic acid with an alcohol to dehydrating reaction in the presence of an acid catalyst; and a method of transesterification by subjecting a cyanoacetic acid ester with an alcohol.

For example, as to methods for preparing t-butyl cyanoacetate, there have been known: ① a method of reacting t-butyl chloroacetate with NaCN or KCN [DE-1951032; Helv. Chim. Acta., 42, 1214, 1222 (1959); J. Am. Chem. Soc., 64, 2274 (1942)], ② a method of reacting a cyanoacetyl halide with t-butanol and N,N-dimethylaniline [J. Chem. Soc., (1955), 423, 426; Org. Synth., Coll. Vol. 5, 171]; and ③ an alkoxycarbonylation method by reacting chloroacetonitrile with CO and t-butanol [DE-2403483].

However, the method of ① requires t-butyl chloroacetate as the raw material, which is not easily available and should be prepared separately through a complicated route. Furthermore, according to this method, there is troublesome problem that a large amount of waste matter such as NaCl, a by-product of the reaction, is produced. Also, the method of ② uses necessarily $PCl_5$, which is highly corrosive compound, for obtaining cyanoacetyl halide as the raw material, and for this reason the construction materials of the equipment for producing the same are greatly restricted. Additionally, an equimolar or excess quantity of N,N-dimethylaniline is required to an equimolar quantity of cyanoacetyl halide. In accordance with proceeding of the reaction, the hydrochloride of N,N-dimethylaniline is by-produced and also a large quantity of other waste matter in produced. Furthermore, the method of ③ is restricted greatly with respect to the equipment for the reason that CO should be reacted under a high pressure.

The method of dehydrating reaction by subjecting cyanoacetic acid with an alcohol in the presence of an acid catalyst is disclosed in some literatures, for example, Ann. Chim., (Paris), 9 (9), 69 (1918); and Tetrahedron, 305, (1967). The reactivity of this method is excellent when an alcohol having a small number of carbon atoms, especially a primary alcohol is used. However, this method shows drawback that the reactivity is lowered when a higher alcohol or tertiary alcohol is used. Furthermore, this method is not adapted for preparing a tertiary ester of cyanoacetic acid which is unstable to an acid.

Additionally, as to the methods of transesterification of a cyanoacetic ester with an alcohol, use of a titanium alkoxide as a catalyst is known [Org. Synth., 65, 230, (1987); Helv. Chim. Acta., 65, 1197, (1982); Helv. Chim. Acta., 65, 495, (1982); and Synthesis, (1982), 138]. However, these literatures indeed disclose reactions by using alcohols such as primary or secondary alcohols, such as methanol, ethanol and isopropanol; but these literatures do not disclose a reaction by using a tertiary alcohol such as t-butanol or the like, which is known to be unsuitable for the transesterification. There have not been found any literature which discloses a transesterification between a cyanoacetic acid ester and t-butanol.

The present invention have been completed to solve the above-mentioned various problems in the prior art, and an object thereof is to prepare cyanoacetic acid higher esters in higher yield by using cyanoacetic acid esters and alcohols as the raw materials which are less expensive and easily available.

DISCLOSURE OF THE INVENTION

The present inventors have studied deligently for the purpose of achieving the above-described object of the invention and, as a result, found that specific tin compounds perform an outstanding catalytic activity in the transesterification between a cyanoacetic acid ester and an alcohol. Thus, the present invention have successfully been made on the basis of such finding.

Thus, the present invention relates to a method for preparing cyanoacetic acid higher esters represented by the general formula: $NCCH_2COOR'$, wherein R' is an alkyl group having 4 to 20 carbon atoms, comprising subjecting a cyanoacetic acid ester represented by the general formula: $NCCH_2COOR^1$, wherein $R^1$ is an alkyl group having 1 to 3 carbon atoms, with an alcohol represented by the general formula: R'OH, wherein R' is an alkyl group having 4 to 20 carbon atoms, to a transesterification reaction in the presence of at least one selected from tin compounds represented by the following formulae (1) to (4) as a catalyst.

wherein $R^2$ and $R^3$ are each independently an alkyl group having 1 to 18 carbon atoms; and $X^1$ and $X^2$ are each —H, —$R^6$, —$OR^6$, —$OCOR^6$, —OCOCH=CHCOO$R^6$, wherein $R^6$ is an alkyl group having 1 to 18 carbon atoms, or a halogen atom,

wherein $R^2$ and $R^3$ are each independently an alkyl group having 1 to 18 carbon atoms,

wherein $R^2$ and $R^3$ are each independently an alkyl group having 1 to 18 carbon atoms; and A is —COCH=CHCO—, and

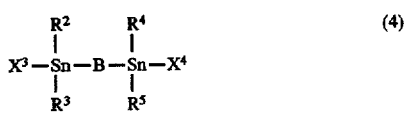

wherein $R^2$, $R^3$, $R^4$ and $R^5$ are each independently an alkyl group having 1 to 18 carbon atoms; $X^3$ and $X^4$ are each independently —$R^6$ or —$OR^6$, wherein $R^6$ is an alkyl group having 1 to 18 carbon atoms; and B is —OCOCH=COO— or —O—.

The present invention will be explained in detail as follows.

The cyanoacetic acid ester used as a raw material in the present invention is represented by the general formula: $NCCH_2COOR^1$, wherein $R^1$ is an alkyl group having 1 to 3 carbon atoms, and specifically includes methyl cyanoacetate, ethyl cyanoacetate, propyl cyanoacetate and isopropyl cyanoacetate.

The alcohol represented by the general formula: R'OH, wherein R' is an alkyl group having 4 to 20 carbon atoms, used in the present invention, includes n-butanol, isobutanol, t-butanol, 1-pentanol, 2-pentanol, 3-pentanol, 2-methyl-1-butanol, 3-methyl-1-butanol, 2-methyl-2-butanol, 3-methyl-2-butanol, 2,2-dimethyl-1-propanol, cyclopentanol, 1-hexanol, 2-hexanol, 3-hexanol, 4-methyl-1-pentanol, 4-methyl-2-pentanol, 3-methyl-3-methnaol, 2,3-dimethyl-2-butanol, 3,3-dimethyl-2-butanol, cyclohexanol, 1-heptanol, 2-heptanol, 3-heptanol, 4-heptanol, 3-ethyl-3-pentanol, 2,4-dimethyl-3-pentanol, 2,3,3-trimethyl-2-butanol, 1-octanol, 2-octanol, 2-ethyl-1-hexanol, 1,1,3,3-tetramethyl-1-butanol, 1-nonanol, 2-nonanol, 2,6-dimethyl-4-heptanol, 1-decanol, 1-undecanol, 1-dodecanol, 1-tridecanol, 1-tetradecanol, 1-pentadecanol, 1-hexadecanol, 1-heptadecanol, 1-octadecanol, triphenylmethanol and the like.

Specifically, t-butanol, 1-pentanol, 1-hexanol, cyclopentanol, cyclohexanol and the like may preferably be used.

With respect to the used amounts of the cyanoacetic acid ester and the alcohol as the raw materials, the alcohol may be used generally in a range of 1.5 to 30 times of molar quantity, preferably in a range of 2 to 20 times of molar quantity, per mole of the cyanoacetic acid ester.

The reaction of a cyanoacetic acid ester with an alcohol is carried out in the presence of a tin compound as a catalyst.

As to the tin compounds, any one of tin compounds represented by the following formulae (1) to (4) is used.

wherein $R^2$ and $R^3$ are each an alkyl group having 1 to 18 carbon atoms; $X^1$ and $X^2$ are each —H, —$R^6$, —$OR^6$, —$OCOR^6$, —OCOCH=CHCOO$R^6$, wherein $R^6$ is an alkyl group having 1 to 18 carbon atoms, or a halogen atom.

The tin compound of the formula (1) includes dibutyltin dimethoxide, dibutyltin diethoxide, dioctyltin dimethoxide, dioctyltin diethoxide, dibutyltin di(t-butoxide), dioctyltin di(t-butoxide), dibutyltin dihydride, dioctyltin dihydride, dibutyltin diacetate, dioctyltin diacetate, dibutyltin dioctate, dioctyltin dioctate, dibutyltin dilaurate, dioctyltin dilaurate, dibutyltin distearate, dioctyltin distearate, tributyltin acetate, trioctyltin acetate, tributyltin octate, trioctyltin octate, tributyltin laurate, trioctyltin laurate, tributyltin stearate, trioctyltin stearate, tributyltin methoxide, trioctyltin methoxide, tributyltin ethoxide, trioctyltin ethoxide, tributyltin t-butoxide, trioctyltin t-butoxide, dibutyltin bis (monomethylmaleate), dioctyltin bis(monomethylmaleate), dibutyltin bis(monooctylmaleate), dioctyltin bis (monooctylmaleate), dibutyltin bis(monolaurylmaleate), dioctyltin bis(monolaurylmaleate), dibutyltin dichloride, dioctyltin dichloride and the like.

Specifically, dibutyltin dimethoxide, dibutyltin diethoxide, dioctyltin dimethoxide, dioctyltin diethoxide, dibutyltin di(t-butoxide), dioctyltin di(t-butoxide), dibutyltin dihydride, dioctyltin dihydride, dibutyltin diacetate, dioctyltin diacetate, dibutyltin dioctate, dioctyltin dioctate, dibutyltin dilaurate, dioctyltin dilaurate, dibutyltin distearate, dioctyltin distearate, tributyltin methoxide, trioctyltin methoxide, tributyltin t-butoxide, trioctyltin t-butoxide and the like may be preferably used.

wherein $R^2$ and $R^3$ are each an alkyl group having 1 to 18 carbon atoms.

The tin compound of the formula (2) includes dibutyltin oxide, dioctyltin oxide, dicyclohexyltin oxide and the like. Specifically, dibutyltin oxide, dioctyltin oxide may preferably be used.

wherein $R^2$ and $R^3$ are each an alkyl group having 1 to 18 carbon atoms; and A is —COCH=CHCO—, The tin compound of the formula (3) includes dibutyltin maleate and dioctyltin maleate.

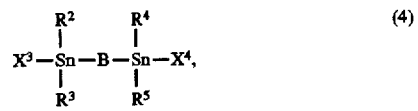

wherein $R^2$, $R^3$, $R^4$ and $R^5$ are each an alkyl group having 1 to 18 carbon atoms; $X^3$ and $X^4$ are each —$R^6$ or —$OR^6$, wherein $R^6$ is an alkyl group having 1 to 18 carbon atoms; and B is —OCOCH=CH—COO— or —O—.

The tin compound of the formula (4) includes bis (tributyltin) oxide, bis(tri-octyltin) oxide, bis(tributyltin) maleate, bis(trioctyltin) maleate, bis(dibutylmethoxytin) maleate, bis(dioctylmethoxytin) maleate, bis (dibutylmethoxytin) oxide, bis(dioctylmethoxytin) oxide, bis{dibutyl(t-butoxy)tin} maleate, bis{dioctyl(t-butoxy)tin} maleate, bis{dibutyl(t-butoxy)tin} oxide, bis{dioctyl(t-butoxy)tin} oxide, bis(dibutyllauroxytin) maleate, bis (dioctyllauroxytin) maleate, bis(dibutyllauroxytin) oxide, bis(dioctyllauroxytin) oxide and the like.

Specifically, bis(dibutylmethoxytin) maleate, bis (dioctylmethoxytin) maleate, bis(dibutylmethoxytin) oxide, bis(dioctylmethoxytin) oxide, bis{dibutyl(t-butoxy)tin} maleate, bis{dioctyl(t-butoxy)tin} maleate, bis{di-butyl(t-butoxy)tin} oxide and bis{dioctyl(t-butoxy)tin} oxide may be preferably used.

Since the above-mentioned catalysts which are used in the methods of the present invention are dissolved in the reactive raw materials, their catalytic activity appear quickly, so that the reaction rate can be increased remarkably. Furthermore, the activity of the above-mentioned catalysts is hardly decreased during the reaction. The reaction can be simply carried out since the catalyst may be added to the reaction system in one time at the beginning of the reaction.

Also, the activity of these catalysts, as compared with conventional catalysts, is only affected slightly even though trace amount of water is present in the reaction system. Therefore, the trace amount of water need not be completely removed from the reaction system. Furthermore, the tin compounds as these catalysts are usually economically and easily available because they are used as stabilizers for vinyl chloride resins and as agricultural chemicals, and are used as raw material for preparing the same.

The amount of the above-mentioned catalysts used may be within a range of 0.1 to 50 mol %, preferably 0.5 to 25 mol % to the cyanoacetic acid ester.

The reaction temperature in the methods of the present invention is selected from within a range of 40° to 250° C., preferably within a range of 60° to 200° C. The reaction time varies depending on reaction conditions such as the molar ratio of the raw materials, the amount of catalyst, and the reaction temperature, and is generally within 12 hours, and is selected from within a range of 3 to 10 hours.

The reaction can be carried out under any of ordinary pressure, reduced pressure and increased pressure, and the reaction can be advantageously carried out by removing the by-produced alcohol quickly from the reaction system by distillation. The alcohol which is by-produced in the reaction is introduced to a distillation tower, and removal of the alcohol is efficiently conducted by taking it out from the reaction system during reflux in a suitable refluxing ratio of the reaction system. In this case, the refluxing ratio may be selected suitably from within a range of 1:1 to 30:1, generally within a range of 1:1 to 15:1.

Generally, there is no necessity to use any solvent in this reaction. However, use of a solvent may be allowable. As to type of the usable solvents, benzene, toluene and xylene may be mentioned.

The general embodiments of the present invention are explained below.

Into a reaction vessel which is equipped with a thermometer and a distillation tower, the predetermined amounts of raw materials: a cyanoacetic acid ester $NCCH_2COOR^1$, wherein $R^1$ represents an alkyl group having 1 to 3 carbon atoms, an alcohol R'OH, wherein R' represents an alkyl group having 4 to 20 carbon atoms, and a catalyst, and a solvent if necessary, are charged. These materials are reacted by heating under fully refluxing conditions for a while, then at the time the refluxing state becomes vigorous, the by-produced alcohol is taken out from the reaction system under the predetermined refluxing ratio.

After the reaction, an excess amount of the raw material alcohol R'OH, wherein R' represents an alkyl group having 4 to 20 carbon atoms, is removed by distillation under reduced pressure by a conventional manner, and the objective product, a cyanoacetic acid higher ester of the formula: $NCCH_2COOR'$, wherein R' represents an alkyl group having 4 to 20 carbon atoms, is then obtained by distillation.

THE BEST MODE FOR CARRYING OUT THE INVENTION

Next, the present invention will be explained more concretely with reference to the following Examples, but the present invention may not be restricted thereby.

EXAMPLE 1

Into a flask which is equipped with a stirrer, a thermometer and a MacMahon packing tower, 9.9 g of methyl cyanoacetate, 74 g of t-butanol and 1.5 g of dibutyltin dimethoxide were added, and these materials were refluxed at 110° C. by heating. After the reaction mixture was fully refluxed for 10 minutes, the reaction was continued while removing the formed methanol from the reaction system by distillation in a refluxing ratio of 10:1. The reaction was carried out for 8 hours by keeping the temperature at the top of the distillation tower around 80° to 85° C.

After the reaction, as the result of analysis of the reaction mixture by means of a gas chromatography, the conversion of methyl cyanoacetate was 95%, and the selectivity of t-butyl cyanoacetate was 100%.

EXAMPLE 2

By using the reaction apparatus used in Example 1, 11.3 g of ethyl cyanoacetate, 65 g of t-butanol and 1.5 g of dibutyltin di(t-butoxide) were heated at 120° C. and the reaction mixture was refluxed. The reaction was carried out for 8 hours while removing the formed ethanol from the reaction system by distillation.

After the reaction, as the result of analysis of the reaction mixture by a gas chromatography, the conversion of ethyl cyanoacetate was 93%, and the selectivity of t-butyl cyanoacetate was 100%.

EXAMPLE 3

By using the reaction apparatus used in Example 1, 9.9 g of methyl cyanoacetate, 75 g cyclohexanol and 1.6 g of dibutyltin dimethoxide were heated at 160° C. and the reaction mixture was refluxed. The reaction was carried out for 8 hours while removing the formed methanol from the reaction system.

After the reaction, as the result of analysis of the reaction mixture by a gas chromatography, the conversion of methyl cyanoacetate was 95%, and the selectivity of cyclohexyl cyanoacetate was 100%.

EXAMPLE 4

By using the reaction apparatus used in Example 1, 11.3 g of ethyl cyanoacetate, 65 g cyclopentanol, and 1.5 g of dibutyltin oxide were heated at 160° C. and the reaction mixture was refluxed. The reaction was carried out for 8 hours while removing the formed ethanol from the reaction system.

After the reaction, as the result of analysis of the reaction mixture by a gas chromatography, the conversion of ethyl cyanoacetate was 93%, and the selectivity of cyclopentyl cyanoacetate was 100%.

EXAMPLE 5

The reaction was carried out in the same manner as in Example 1 but using 80 g of 1-hexanol in place of t-butanol.

After the reaction, as the result of analysis of the reaction mixture by a gas chromatography, the conversion of methyl cyanoacetate was 98%, and the selectivity of (1-hexyl) cyanoacetate was 98%.

EXAMPLE 6

The reaction was carried out in the same manner as in Example 1 but using 1.7 g of dibutyltin diethoxide in place of dibutyltin dimethoxide, and 68 g of 1-pentanol in place of 1-hexanol.

After the reaction, as the result of analysis of the reaction mixture by a gas chromatography, the conversion of methyl cyanoacetate was 98%, and the selectivity of (1-pentyl) cyanoacetate was 99%.

EXAMPLES 7–14

The reactions were carried out in the same manner as in Example 1, except that the catalyst were replaced by those

TABLE 1

| Example No. | Catalyst | (g) | Reaction time (hr) | Conversion (%) | Selectivity (%) |
|---|---|---|---|---|---|
| 7 | Dioctyltin dimethoxide | 1.5 | 8 | 95 | 100 |
| 8 | Dioctyltin diethoxide | 1.5 | 8 | 93 | 100 |
| 9 | Dibutyltin (t-butoxide) | 1.5 | 8 | 98 | 100 |
| 10 | Dioctyltin (t-butoxide) | 1.5 | 8 | 96 | 100 |
| 11 | Dibutyltin dihydride | 2.0 | 10 | 92 | 100 |
| 12 | Dioctyltin dihydride | 2.0 | 10 | 90 | 90 |
| 13 | Dibutyltin oxide | 2.5 | 10 | 88 | 100 |
| 14 | Dioctyltin oxide | 1.5 | 10 | 80 | 100 |

EXAMPLES 15–24

The reactions were carried out in the same manner as in Example 1, except that the catalysts were replaced by those shown in Table 2 and the reaction temperature was set at 130° C. The results are shown in Table 2.

TABLE 2

| Example No. | Catalyst | (g) | Reaction time (hr) | Conversion (%) | Selectivity (%) |
|---|---|---|---|---|---|
| 15 | Dibutyltin diacetate | 5.0 | 10 | 70 | 92 |
| 16 | Dioctyltin diacetate | 5.0 | 10 | 70 | 90 |
| 17 | Dibutyltin dioctate | 5.0 | 10 | 85 | 93 |
| 18 | Dioctyltin dioctate | 5.0 | 10 | 83 | 93 |
| 19 | Dibutyltin dilaurate | 5.0 | 10 | 88 | 93 |
| 20 | Dioctyltin dilaurate | 5.0 | 10 | 88 | 92 |
| 21 | Dibutyltin distearate | 5.0 | 10 | 87 | 91 |
| 22 | Dioctyltin distearate | 5.0 | 10 | 86 | 94 |
| 23 | Dibutyltin maleate | 5.5 | 10 | 85 | 95 |
| 24 | Dioctyltin maleate | 5.5 | 10 | 85 | 95 |

EXAMPLES 25–36

The reactions were carried out in the same manner as in Example 2, except that the catalyst were replaced by those shown in Table 3. The results are shown in Table 3.

TABLE 3

| Example No. | Catalyst | (g) | Reaction time (hr) | Conversion (%) | Selectivity (%) |
|---|---|---|---|---|---|
| 25 | Bis(dibutylmethoxy tin)maleate | 8.0 | 9 | 86 | 89 |
| 26 | Bis(dioctylmethoxy tin)maleate | 8.0 | 9 | 84 | 88 |
| 27 | Bis(dibutylmethoxy tin)oxide | 8.0 | 9 | 80 | 82 |
| 28 | Bis(dioctylmethoxy tin)oxide | 8.0 | 9 | 80 | 83 |
| 29 | Bis[dibutyl(t-butoxy)tin]maleate | 9.0 | 7 | 85 | 90 |
| 30 | Bis[dioctl(t-butoxy)tin]maleate | 9.0 | 7 | 83 | 92 |
| 31 | Bis[dibutyl(t-butoxy)tin oxide | 9.0 | 8 | 82 | 91 |
| 32 | Bis[dioctyl(t-butoxy)tin oxide | 9.0 | 8 | 81 | 93 |
| 33 | Tributyltin methoxide | 5.0 | 10 | 83 | 98 |
| 34 | Trioctyltin methoxide | 5.0 | 10 | 80 | 96 |
| 35 | Tributyltin t-butoxide | 5.5 | 10 | 83 | 95 |
| 36 | Trioctyltin t-butoxide | 5.5 | 10 | 82 | 94 |

INDUSTRIAL APPLICABILITY

According to the methods of the present invention, an alcohol represented by the general formula: R'OH, wherein R' represents an alkyl group having 4 to 20 carbon atoms, which have been known to be unsuitable for transesterification, can be subjected to the transesterification with a cyanoacetic acid ester represented by the general formula: $NCCH_2COOR^1$, wherein $R^1$ represents an alkyl group having 1 to 3 carbon atom, in the presence of a specific tin compound as the catalyst, and a cyanoacetic acid higher ester represented by the general formula: $NCCH_2COOR'$, wherein R' represents an alkyl group having 4 to 20 carbon atoms, in high yield. Furthermore, the objective product thus prepared can be easily purified because by-products are formed in this reaction only in small quantity, therefore the amounts of waste matter in this reaction can be greatly reduced.

We claim:

1. A method for preparing a cyanoacetic acid higher ester of the formula $NCCH_2COOR'$, wherein R' is an alkyl group having 4 to 20 carbon atoms, comprising subjecting a cyanoacetic acid ester of the formula: $NCCH_2COOR^1$, wherein $R^1$ is an alkyl group having 1 to 3 carbon atoms, with an alcohol of the formula: R'OH, wherein R' is an alkyl group having 4 to 20 carbon atoms, to a transesterification reaction in the presence of at least one selected from tin compounds represented by the following formulae (1), (3) and (4) as a catalyst:

(1)

wherein $R^2$ and $R^3$ are each independently an alkyl group having 1 to 18 carbon atoms; and $X^1$ and $X^2$ are each independently $-H$, $-R^6$, $-OR^6$, $-OCOR^6$, $-OCOCH=CHCOOR^6$, wherein $R^6$ is an alkyl group having 1 to 18 carbon atoms, or a halogen atom

(3)

wherein $R^2$ and $R^3$ are each independently an alkyl group having 1 to 18 carbon atoms; and A is $-COCH=CHCO$, and

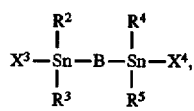

wherein $R^2$, $R^3$, $R^4$ and $R^5$ are each independently an alkyl group having 1 to 18 carbon atoms; $X^3$ and $X^4$ are each independently —$R^6$ or —$OR^6$, wherein $R^6$ is an alkyl group having 1 to 18 carbon atoms; and B is —OCOCH=CH—COO— or —O—.

2. The method for preparing a cyanoacetic acid higher ester according to claim 1, wherein the tin compound of the formula (1) is at least one selected from the group consisting of dibutyltin dimethoxide, dibutyltin diethoxide, dioctyltin dimethoxide, dioctyltin diethoxide, dibutyltin di(t-butoxide), dioctyltin di(t-butoxide), dibutyltin dihydride, dioctyltin dihydride, dibutyltin diacetate, dioctyltin diacetate, dibutyltin dioctate, dioctyltin dioctate, dibutyltin dilaurate, dioctyltin dilaurate, dibutyltin distearate, dioctyltin distearate, tributyltin acetate, trioctyltin acetate, tributyltin octate, trioctyltin octate, tributyltin laurate, trioctyltin laurate, tributyltin stearate, trioctyltin stearate, tributyltin methoxide, trioctyltin methoxide, tributyltin ethoxide, trioctyltin ethoxide, tributyltin t-butoxide, trioctyltin t-butoxide, dibutyltin bis(monomethylmaleate), dioctyltin bis(monomethylmaleate), dibutyltin bis(monooctylmaleate), dioctyltin bis(monooctylmaleate), dibutyltin bis(monolaurylmaleate), dioctyltin bis(monolaurylmaleate), dibutyltin dichloride, and dioctyltin dichloride.

3. The method for preparing a cyanoacetic acid higher ester according to claim 1, wherein the tin compound of the formula (3) is at least one selected from the group consisting of dibutyltin maleate and dioctyltin maleate.

4. The method for preparing a cyanoacetic acid higher ester according to claim 1, wherein the tin compound of the formula (4) is at least one selected from the group consisting of bis(tributyltin) oxide, bis(trioctyltin) oxide, bis(tributyltin) maleate, bis(trioctyltin) maleate, bis(dibutylmethoxytin) maleate, bis(dioctylmethoxytin) maleate, bis(dibutylmethoxytin) oxide, bis(dioctylmethoxytin) oxide, bis{dibutyl(t-butoxy)tin} maleate, bis{dioctyl-(t-butoxy)tin} maleate, bis{dibutyl(t-butoxy)tin} oxide, bis{dioctyl(t-butoxy)tin} oxide, bis(dibutyllauroxytin) maleate, bis(dioctyllauroxytin) maleate, bis(dibutyllauroxytin) oxide and bis(dioctyllauroxytin) oxide.

5. The method for preparing a cyanoacetic acid higher ester according to claim 1, wherein R' is t-butyl, 1-pentyl, 1-hexyl, cyclopentyl or cyclohexyl group.

* * * * *